(12) United States Patent
Wang et al.

(10) Patent No.: US 7,816,461 B2
(45) Date of Patent: Oct. 19, 2010

(54) BLOCK COPOLYMERS OF POLYCARPOLACTONE AND POLY (PROPYLENE FUNARATE)

(76) Inventors: Shanfeng Wang, 1517 41st St. NW., Rochester, MN (US) 55901; Michael J. Yaszemski, 2806 15th Ave. SW., Rochester, MN (US) 55902; Lichun Lu, 734 27th St. NW., Rochester, MN (US) 55901; Bradford L. Currier, 2005 Merrihills Dr. SW., Rochester, MN (US) 55902

( * ) Notice: Subject to any disclaimer, the term of this patent is extended or adjusted under 35 U.S.C. 154(b) by 357 days.

(21) Appl. No.: 11/718,962

(22) PCT Filed: Nov. 18, 2005

(86) PCT No.: PCT/US2005/042240

§ 371 (c)(1),
(2), (4) Date: May 9, 2007

(87) PCT Pub. No.: WO2006/055940

PCT Pub. Date: May 26, 2006

(65) Prior Publication Data

US 2008/0004368 A1    Jan. 3, 2008

Related U.S. Application Data

(60) Provisional application No. 60/629,198, filed on Nov. 18, 2004.

(51) Int. Cl.
C08G 63/91    (2006.01)

(52) U.S. Cl. .................. 525/411; 525/408; 525/419; 525/420; 525/437; 525/444; 525/450; 424/426; 424/78.08; 424/486; 424/488; 623/16.11; 623/17.11; 623/11.11; 523/113; 523/114; 523/115; 523/116; 523/124; 523/125

(58) Field of Classification Search .................. 525/411, 525/444, 408, 419, 420, 437, 450; 523/113, 523/116, 114, 115, 124, 125; 424/78.08, 424/486, 488; 623/16.11, 17.11, 11.11; 435/174, 435/180; 528/354, 272, 361

See application file for complete search history.

(56) References Cited

U.S. PATENT DOCUMENTS

| | | | |
|---|---|---|---|
| 5,527,864 A | 6/1996 | Suggs et al. | |
| 5,644,005 A | 7/1997 | Suggs et al. | |
| 5,733,951 A | 3/1998 | Yaszemski et al. | |
| 5,869,170 A | 2/1999 | Cima et al. | |

(Continued)

OTHER PUBLICATIONS

Fisher, John et al., Photoinitiated Cross-linking of the biodegradable polyester poly(propylene fumarate). Part I. Determination of Network Structure . . . , Jun. 10, 2003, Biomacromolecules 2003, 4, 1327-1334.*

(Continued)

Primary Examiner—Milton I Cano
Assistant Examiner—Michael Leonard

(57) ABSTRACT

Poly(propylene fumarate) is copolymerized with poly(caprolactone) diol to produce a block copolymer of poly(propylene fumarate) and poly(caprolactone). The biocompatible and bioresorbable block copolymer of poly(propylene fumarate) and poly(caprolactone) is useful in the fabrication of injectable and in-situ hardening scaffolds for tissue and/or skeletal reconstruction. The block copolymer can be crosslinked by redox or photo-initiation, with or without an additional crosslinker. Thus, the copolymer is both self-crosslinkable (without the use of any crosslinkers) and photocrosslinkable (in the presence of photons such as UV light).

17 Claims, 8 Drawing Sheets

U.S. PATENT DOCUMENTS

| | | | |
|---|---|---|---|
| 6,124,373 | A | 9/2000 | Peter et al. |
| 6,379,962 | B1 | 4/2002 | Holy et al. |
| 6,436,426 | B1 | 8/2002 | Liao et al. |
| 6,753,358 | B2 | 6/2004 | Fisher et al. |
| 6,884,432 | B2 | 4/2005 | Yaszemski et al. |
| 6,884,778 | B2 | 4/2005 | Jo et al. |
| 2001/0039453 | A1* | 11/2001 | Gresser et al. ............ 623/17.11 |
| 2001/0048945 | A1* | 12/2001 | Sankaram .................... 424/469 |
| 2002/0028189 | A1* | 3/2002 | Jo et al. ...................... 424/78.3 |
| 2003/0152548 | A1* | 8/2003 | Mikos et al. ............. 424/78.26 |
| 2004/0054410 | A1 | 3/2004 | Barrows |
| 2005/0209704 | A1* | 9/2005 | Maspero et al. ............ 623/23.5 |
| 2008/0194792 | A1* | 8/2008 | Wang et al. ................. 528/275 |

OTHER PUBLICATIONS

Kweon, HaeYong et al., A novel degradable polycarprolactone networks for tissue engineering. Biomaterials 24 (2003), 801-808.*

International Search Report and Written Opinion Under Date of Mailing of Jun. 21, 2006, in connection with International Patent Application No. PCT/US2005/042220.

* cited by examiner

BLOCK COPOLYMERS OF POLYCARPOLACTONE AND POLY (PROPYLENE FUNARATE)

CROSS-REFERENCES TO RELATED APPLICATIONS

This application claims priority from U.S. Provisional Patent Application No. 60/629,198 filed Nov. 18, 2004. This application is a national stage entry of PCT/US/42240 filed Nov. 18, 2005 now WO-2006/055940 published May 26, 2006.

STATEMENT REGARDING FEDERALLY SPONSORED RESEARCH

This invention was made with government support under grant number AR045871 from the National Institute of Arthritis and Musculoskeletal and Skin Diseases, as well as grant number EB003060 from the National Institute of Biomedical Imaging and Bioengineering. The government has certain rights in the invention.

BACKGROUND OF THE INVENTION

1. Field of the Invention

This invention relates to the synthesis of a block copolymer of poly(caprolactone) and poly(propylene fumarate) useful as a biocompatible, bioresorbable, injectable, and in-situ hardening scaffold for tissue engineering applications. The block copolymer can be crosslinked by redox or photo-initiation, with or without an additional crosslinker. Thus, the copolymer is both self-crosslinkable and photocrosslinkable.

2. Description of the Related Art

The clinical needs for bone regeneration are diverse, and there are roughly 1,000,000 patients who have skeletal defects each year in the United States that require bone graft procedures to achieve union. These include applications arising from resection of primary and metastatic tumors, bone loss after skeletal trauma, primary and revision total joint arthroplasty with bone deficiency, spinal arthrodesis, and trabecular voids following osteoporotic insufficiency fractures. Current clinical decision making in the selection, preparation and application of bone graft materials often involves many factors. From a structural perspective, several decisions need to be addressed prior to deciding on a surgical management plan.

First, the type of bone lost must be determined. The defect may be trabecular bone, cortical bone, or a combination of both structural bone types. Second, the nature of the defect must be defined, whether it is contained and has a bony or soft tissue shell, or is non-contained and represents a segmental loss of bone continuity. Third, the size of the defect (size of trabecular voids or length of segmental defects) must be determined. Mechanical issues that enter into the graft selection decision include the skeletal location of the defect to be reconstructed and the anticipated loads in that location. In addition, biologic issues such as host co-morbidities (for example, diabetes) may all have an effect on the bone graft incorporation process. Finally, surgical issues that play a role in the selection of graft material include consideration regarding the size of the surgical access portal relative to the size of the defect.

Current clinical methods of treating skeletal defects involve bone transplantation or the use of other materials to restore continuity. Autologous bone graft has been the gold standard of bone replacement because it provides such essential elements as osteogenic cells, osteoinductive factors, and an osteoconductive matrix for healing. However, the limited supply of autograft bone, and donor site morbidity both restrict the spectrum of cases in which it can be used alone. Allograft bone, although available in abundant supply, has drawbacks that include reduced rates of graft incorporation compared to autograft bone, and the possibility of pathogen transfer from donor to host.

Metals provide immediate mechanical support at the defect site but exhibit less than ideal overall integration with host tissue and can eventually fail due to fatigue loading if the bone does not heal prior to fatigue failure of the metal. Ceramics, such as β-tricalcium phosphate (β-TCP) and hydroxyapatite are both osteoconductive, and have found clinical use as surface coatings on metal prostheses to enhance bonding of those prostheses to bone. In particulate form, they offer increased mechanical strength to polymeric composite materials primarily in compression, but are less effective in enhancing resistance to torsional and bending forces. Poly (methyl methacrylate) bone cement can be injected or molded and is sometimes used to fill both cavitary and segmental defects, such as those that result from the curettage of a giant cell tumor or from the resection of a vertebral body in metastatic disease to the spine, respectively. However, the temperature can rise up to 100° C. during the exothermic polymerization reaction, and the heat released risks local tissue injury. Additionally, poly(methyl methacrylate) is non-biodegradable and can thus accumulate fatigue damage with time and eventually undergo mechanical failure.

Synthetic biodegradable polymers may provide treatment options not currently available. These materials can be manufactured in virtually unlimited supply and the flexibility in their design allows the synthesis of a wide range of polymers with varying mechanical, biologic, degradation, and rheologic properties. For instance, their mechanical and degradation properties can be manipulated by changing the polymer molecular weight during synthesis, and can thus be tailored to fit a particular application. The injectable nature of the skeletal regeneration biomaterial would be ideal to fill defects with limited accessibility or irregular shape. For example, minimally invasive endoscopic techniques now in clinical use would allow the injectable form of the biomaterial to be inserted for posterolateral intertransverse process spinal fusion. This would decrease the surgical trauma from the extensive exposure and muscle stripping that must now be done to put the graft material into position. The injectable material could be placed into cancellous voids from periarticular fractures, osteoporotic spinal fractures, or bone cysts without creating a large access hole in the surrounding cortical bone. These clinical situations represent the motivation for the development of injectable biodegradable polymeric composite materials for bone tissue engineering.

Thus, biodegradable scaffolds that can be injected and crosslinked in situ to fill defects offer attractive additions to existing methods (see, Yaszemski et al., "Clinical needs for bone tissue engineering technology", in Bone Engineering, J. E. Davis, Ed. Toronto, Em Squared, 2000, pp. 541-547). Recently developed injectable materials have fulfilled many design criteria for diverse orthopaedic applications. A candidate material of this type is poly(propylene fumarate) (PPF), an unsaturated linear polyester that can be modified or crosslinked through its fumarate double bonds. PPF degrades by simple hydrolysis of the ester bonds and the degradation time depends on polymer characteristics such as molecular weight, type of crosslinker, and crosslinking density. Although many efforts have been made to explore the applications of PPF-based materials, there are still many important limitations of this material. The propylene glycol in each repeating unit provides only one free rotating carbon-carbon bond that contributes to the rigidity of the PPF polymer chain. In addition, a crosslinker is needed to form crosslinked PPF networks via redox initiation, which may lead to cytotoxicity associated with unreacted crosslinking monomers.

Poly(ε-caprolactone) (PCL) is a well-known biodegradable polymer and FDA-approved for use as resorbable sutures. It has excellent biocompatibility and flexibility. PCL was recently studied as a potential material for a temporary joint spacer. Also, a copolymer based on PCL and fumarate segments, poly(caprolactone fumarate) (PCLF) has been developed as described in PCT International Patent Application No. WO 2005/004811. Due to the presence of PCL units, the PCLF chain is much more flexible than the PPF chain. This renders PCLF self-crosslinkable without the use of any crosslinkers. Also, the flexibility of PCLF is an advantage in certain applications.

Still, there is a need to improve the mechanical strength and self-crosslinking characteristics of poly(caprolactone fumarate), which is useful as a biocompatible, bioresorbable, injectable, and in-situ hardening scaffold for tissue engineering applications.

SUMMARY OF THE INVENTION

To improve the mechanical strength and self-crosslinking characteristics of poly(caprolactone fumarate), we have developed a novel block copolymer of poly(propylene fumarate) and poly(ε-caprolactone), often hereinafter referred to as P(PF-co-CL). The relatively rigid poly(propylene fumarate) segment provides mechanical strength and crosslinkability while the poly(ε-caprolactone) segment provides flexibility for self-crosslinking. The physical, chemical, mechanical, and degradation properties of P(PF-co-CL) can be modulated by varying the PPF and PCL molecular weight and their relative block lengths. In addition, only PPF and PCLF of relatively low molecular weights ($M_n$<5000 daltons) have been synthesized due to heat-induced crosslinking during polymerization. For the block copolymer of poly(propylene fumarate) and poly(ε-caprolactone), it is possible to achieve a higher molecular weight because the saturated component of PCL in the polymerization lessens the possibility of the crosslinking process of double bonds in PPF segments.

In accordance with the invention, poly(propylene fumarate) is copolymerized with poly(ε-caprolactone). The present invention provides for the synthesis of a block copolymer of poly(propylene fumarate) and poly(ε-caprolactone) which is a biocompatible, bioresorbable, injectable, and self-crosslinkable and/or photocrosslinkable copolymer for bone tissue engineering. The block copolymer of poly(propylene fumarate) and poly(ε-caprolactone) can be physically mixed with other formulation components such as porogen, initiator, crosslinking agent, accelerator, diluent, foaming agent, buffering agent, inhibitor catalyst, growth factors, particulate and fiber reinforcing materials, and stabilizers in free or encapsulated form and the block copolymer of poly(propylene fumarate) and poly(ε-caprolactone) can be injected via a syringe to fabricate a scaffold used for regeneration of biological tissues. Application of this invention can be as an injectable bioresorbable synthetic bone substitute or as an injectable bioresorbable bone cement with controlled degradation behavior.

These and other features, aspects, and advantages of the present invention will become better understood upon consideration of the following detailed description, drawings, and appended claims.

DETAILED DESCRIPTION OF THE INVENTION

The invention provides a block copolymer of poly(propylene fumarate) and poly(ε-caprolactone). The block copolymer is biocompatible, bioresorbable, injectable, and crosslinkable. The block copolymer can be crosslinked by redox or photo-initiation, with or without an additional crosslinker. Thus, the copolymer is both self-crosslinkable (without the use of any crosslinkers) and photocrosslinkable (in the presence of photons such as UV light).

A block copolymer according to the invention includes caprolactone units and propylene fumarate units. In one embodiment, the block copolymer has the following formula:

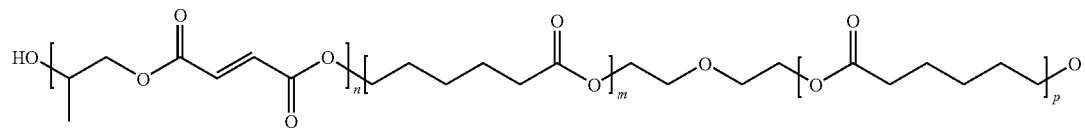

wherein n, m and p are integers. In one example of this embodiment of the block copolymer, n is 1 to 16, m is 5 to 24, and p is 5 to 24. In another example of this embodiment of the block copolymer, the block copolymer has a number average molecular weight of 5000 daltons or greater.

Figure 1:
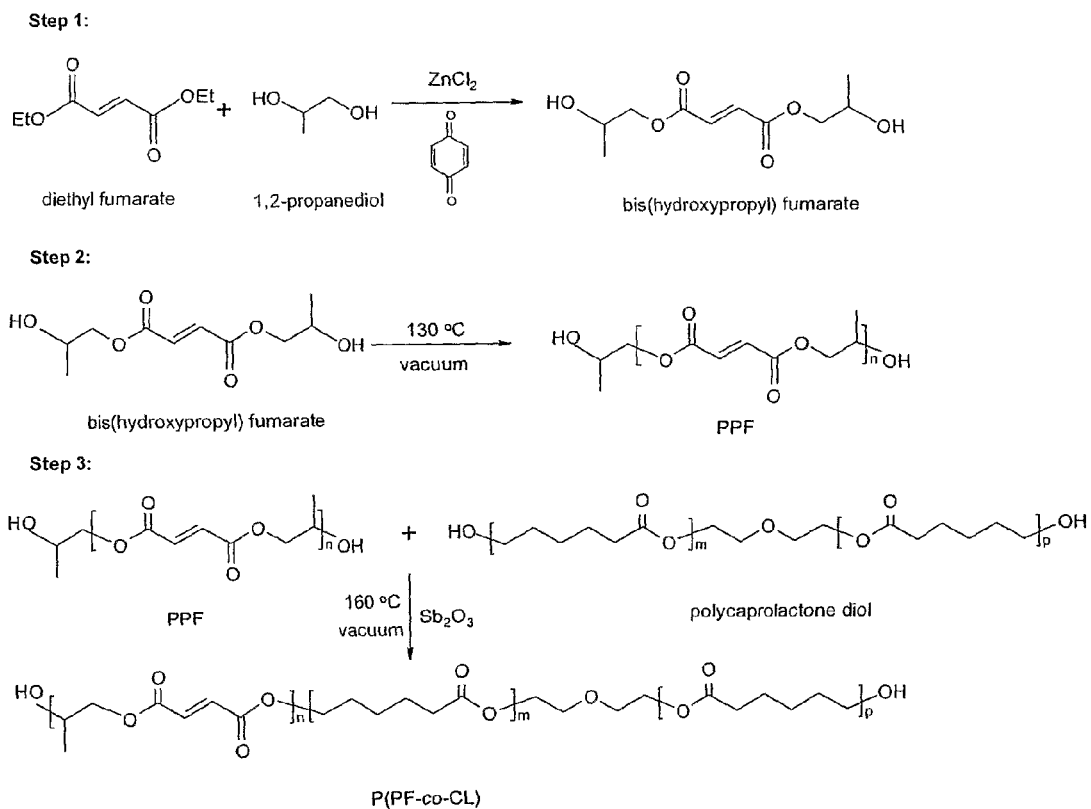
FIG. 1 shows synthesis schemes of a block copolymer of poly(propylene fumarate) and poly(ε-caprolactone) (P(PF-co-CL)).
Figure 2:
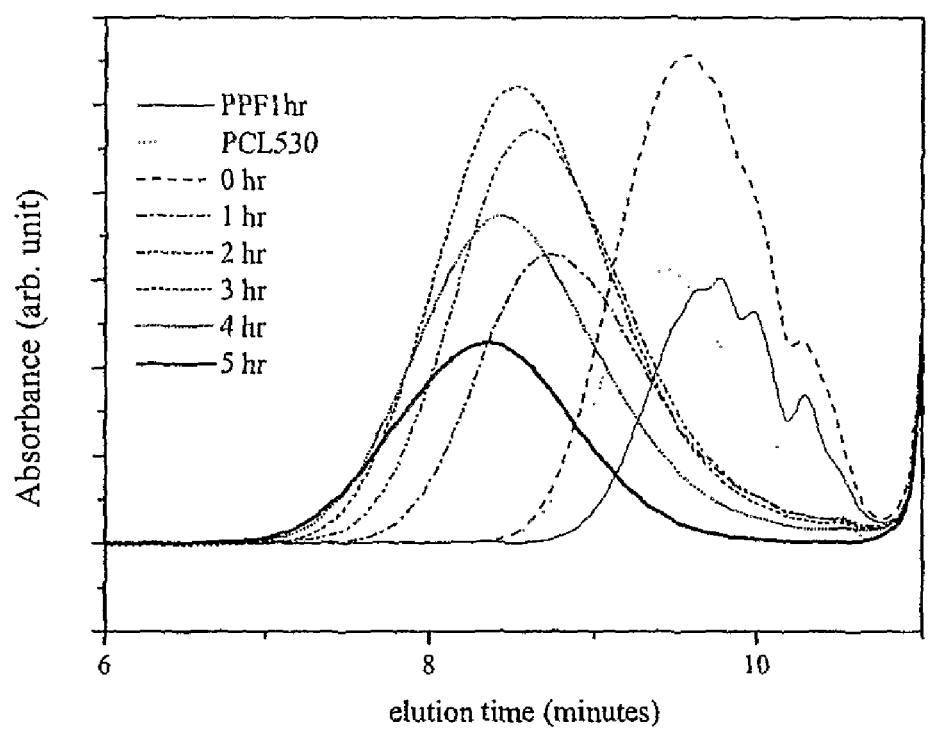
FIG. 2 shows GPC curves of P(PF-co-CL) copolymer 10 at the reaction times of 0-5 hours as well as PCL530 and PPF1hr.
Figure 3:
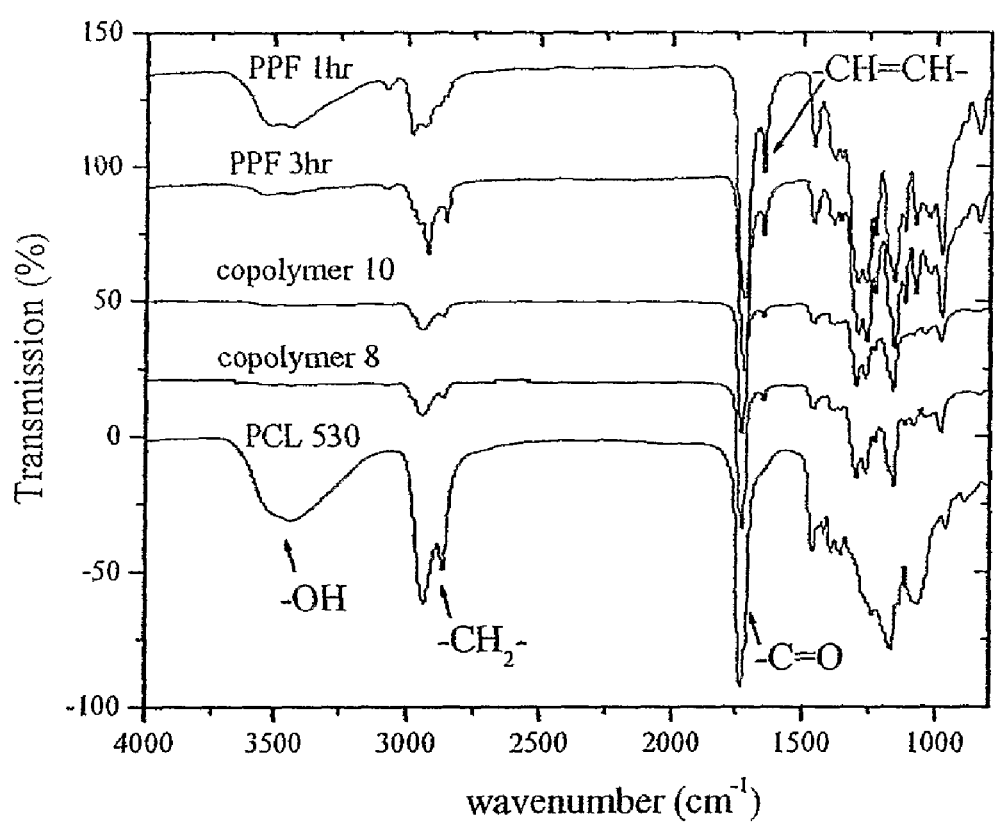
FIG. 3 shows FTIR spectra of oligomeric PPF, PCL530, and P(PF-co-CL) copolymers.
Figure 4:
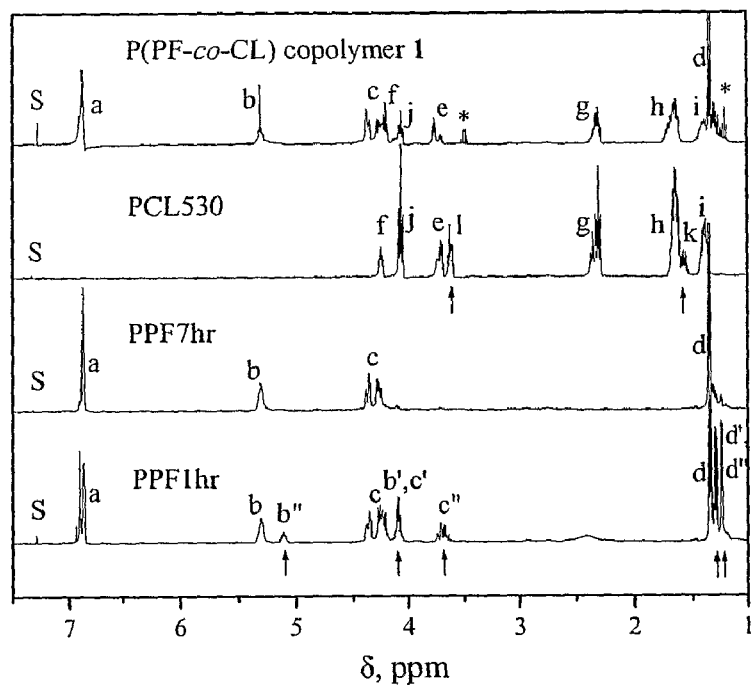
FIG. 4 shows $^1$H NMR (400.1 MHz, CDCl$_3$, reference TMS) spectra of P(PF-co-CL) copolymer 1, PCL530, PPF3000, and PPF1hr. S=solvent. Asterisks indicate signals due to diethyl ether and arrows indicate signals due to protons adjacent to end groups.
Figure 4:
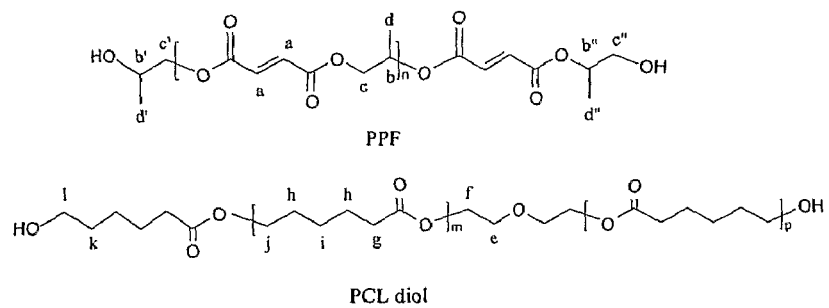
Figure 5:
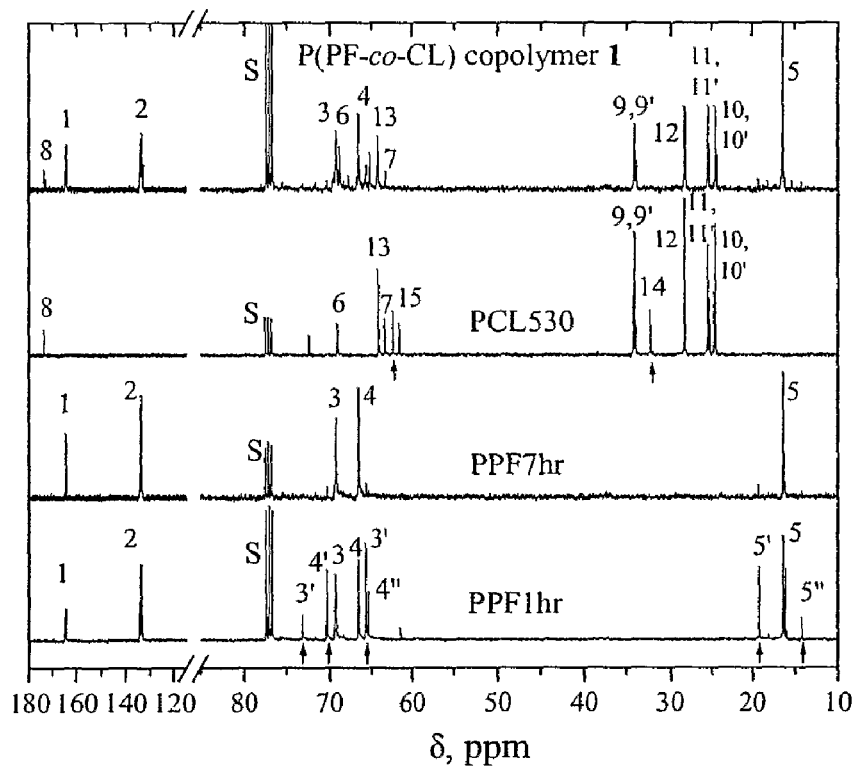
FIG. 5 shows $^{13}$C NMR (100.6 MHz, CDCl$_3$, reference TMS) spectra of P(PF-co-CL) copolymer 1, PCL530, PPF3000, and PPF1hr. S=solvent. Arrows indicate signals due to carbons adjacent to end groups.
Figure 5:
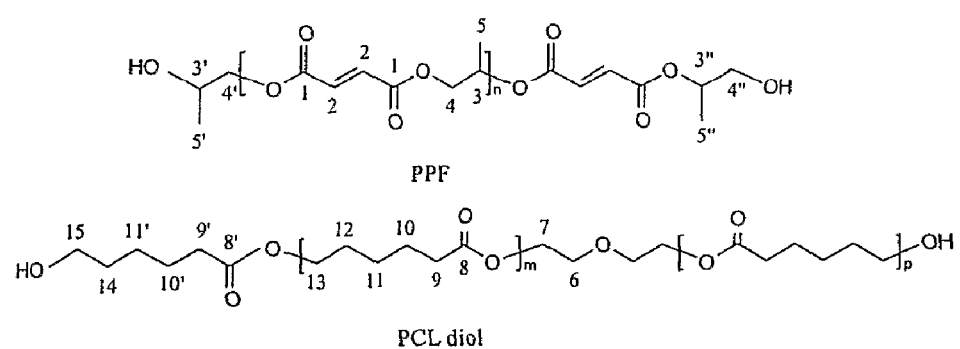
Figure 6:
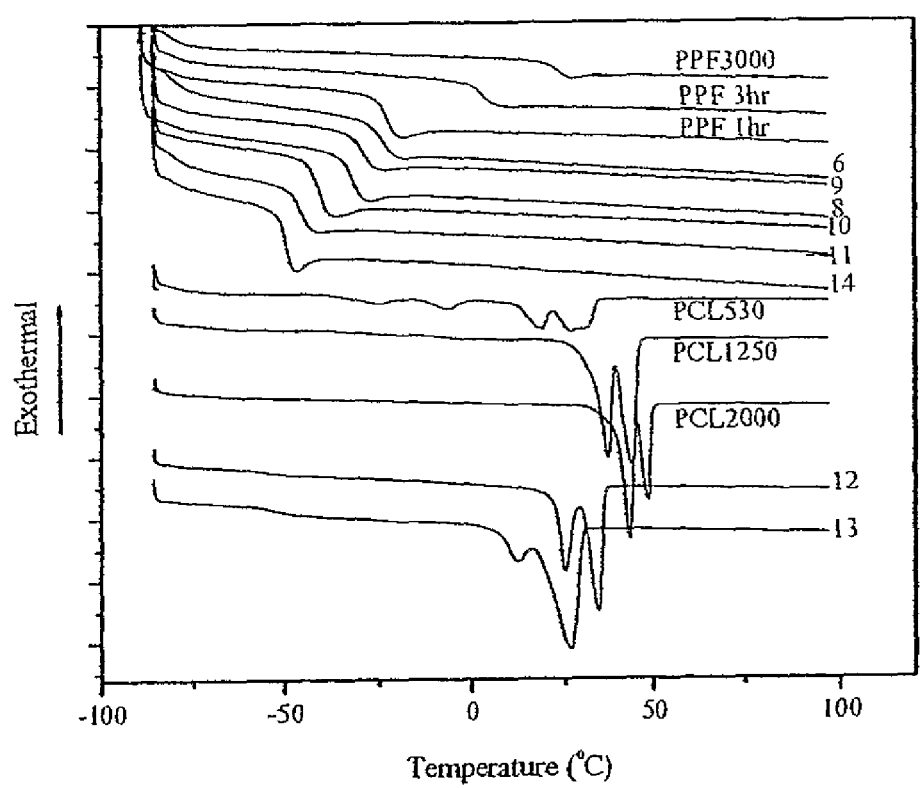
FIG. 6 shows DSC curves of P(PF-co-CL) copolymers, PPF, and PCl diols.
Figure 7:
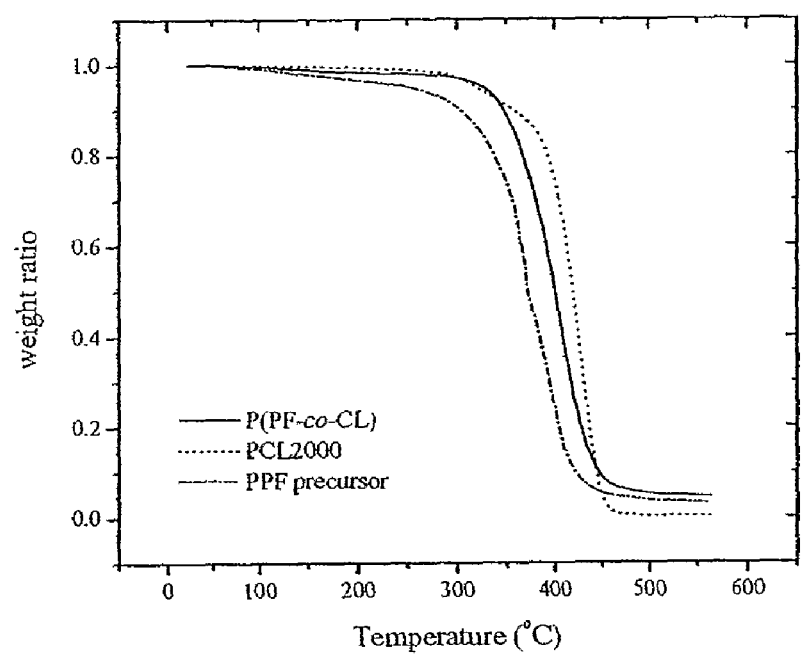
FIG. 7 shows TGA thermograms of oligomeric PPF, PCL 2000, and P(PF-co-CL) copolymer.
Figure 8:
FIG. 8 shows the porous three dimensional structure (pore size: 600 μm., wall thickness: 500 μm.) of two typical copolymer scaffolds (a: copolymer 1; b: copolymer 6) made using solid freeform fabrication (SFF) technique, i.e., 3D printing and injection molding.
Figure 8:
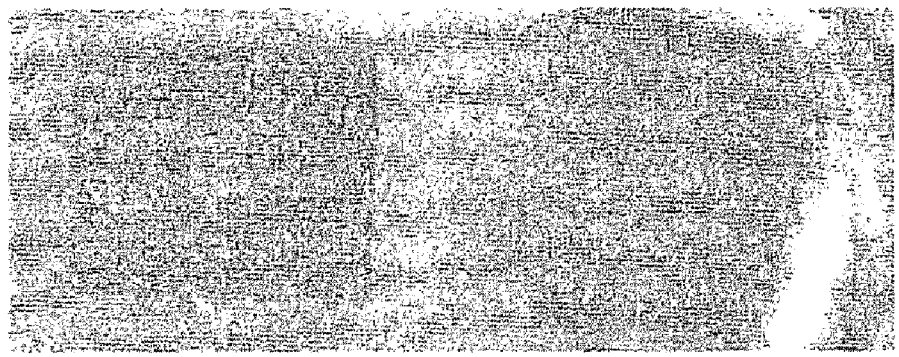

In one method for preparing the block copolymer of poly (propylene fumarate) and poly(ε-caprolactone) as shown in FIG. 1, diethyl fumarate and 1,2-propanediol are mixed together with hydroquinone as a crosslinking inhibitor and zinc chloride as a polymerization catalyst. A bis(hydroxypropyl)fumarate intermediate is formed. The intermediate is transesterified to form linear poly(propylene fumarate) with hydroxyl groups on both ends. The molecular weight of PPF can be modulated by varying the polymerization time. After making the PPF block, the reaction is stopped. To synthesize the block copolymer of poly(ε-caprolactone) and poly(propylene fumarate), polycaprolactone diol and poly(propylene fumarate) are reacted in the presence of antimony trioxide as a catalyst. In one version of the method, the polycaprolactone diol has molecular weight in the range of 500 to 10,000 daltons. A block copolymer of poly(propylene fumarate) and poly(ε-caprolactone) (P(PF-co-CL)) results. The purified product of P(PF-co-CL) is a transparent, light yellow, viscous liquid when PCL content in the copolymers is lower than 70%. Otherwise, it is wax-like at room temperature.

In another aspect, the invention provides a self-crosslinkable and/or photocrosslinkable, biodegradable material including a block copolymer of poly(propylene fumarate) and poly(ε-caprolactone) according to the invention and a free radical initiator or a photoinitiator.

Non-limiting examples of free radical initiators include peroxy compounds (such as diacyl peroxides, e.g. benzoyl peroxide), alkyl hydroperoxide (such as diisopropylbenzene monohydroperoxide), alkyl peresters (such as tert-butyl perbenzoate), dialkyl peroxides (such as di-tert-butyl peroxide), peroxydicarbonates (such as dicetyl peroxide dicarbonate), inorganic peroxides (such as ammonium peroxodisulfate and potassium peroxodisulfate) and azo compounds (such as 2,2'-azobis[N-(2-propenyl)-2-methylpropionamides], 1-[(cyano-1-methylethyl)azo]formamides, 2,2'-azobis(N-butyl-2-methylpropionamides), 2,2'-azobis(N-cyclohexyl-2-methylpropionamides), 2,2'-azobis{2-methyl-N-[2-(1-hydroxybutyl)]propionamides}, 2,2'-azobis{2-methyl-N-[2-(1-hydroxybutyl)]propionamides, 2,2'-azobis{2-methyl-N-[1,1-bis(hydroxymethyl)-2-hydroxyethyl]propionamides, and 2,2'-azobisisobutyronitrile).

Non-limiting examples of photoinitiators include benzoin and benzoin ether compounds, benzil ketal compounds, acetophenone compounds, aminoalkylphenone compounds, hydroxyalkylphenone compounds, acylphosphine oxides, acylphosphine sulfides, phenylglyoxylate compounds, benzophenone compounds, thioxanthone compounds, and mixtures thereof. In one example material, the photoinitiator is bisacylphosphinoxide.

The self-crosslinkable and/or photocrosslinkable, biodegradable material according to the invention may be used as an injectable bone substitute or an injectable bone cement. However, the applications of the material extend beyond scaffolds and bone cement. The self-crosslinkable and/or photocrosslinkable, biodegradable material including a block copolymer of poly(propylene fumarate) and poly(ε-caprolactone) according to the invention is suitable as a crosslinkable polymer in many biomedical applications. Since it is crosslinkable, a micropatterned surface can be made using this material. The material can also form a polymer network with controlled swelling ratios in a variety of solvents which make the material a sorbent for organic solvents or a carrier for catalysts.

With respect to the injectable nature of a block copolymer of poly(propylene fumarate) and poly(ε-caprolactone) according to the invention, the temperature range of injection can be broad, between the melting point of the mixture and the boiling point of the solvent used in the mixture. Normally the polymer mixture is injected at room temperature for convenience. For PPF, one component in the copolymer, the highest temperature during the crosslinking would be around 48° C., while polymethylmethacrylate, the currently used bone cement, may cause as high as 100° C. during crosslinking. Thus, PPF has advantages over polymethylmethacrylate. For the copolymers according to the invention, the temperature would be even lower than 48° C. because the content of PPF, the only crosslinkable segment in copolymers, is lower than 100%.

Because the biodegradable material is self-crosslinking, the material does not need to include a crosslinker. A crosslinker is typically used to help bridge the neighboring double bonds in crosslinking. Because the self-crosslinkable and/or photocrosslinkable, biodegradable material according to the invention does not need any crosslinkers, toxicity concerns in biomedical applications are minimized; however, a crosslinker can be used.

In another form, the self-crosslinkable and/or photocrosslinkable, biodegradable material includes particulate or fiber reinforcement materials. Preferably, the particulate or fiber reinforcement materials comprise a bioactive ceramic such as hydroxyapatite or may comprise single-wall carbon nanotubes.

The material may further include one or more bioactive agents. A "bioactive agent" as used herein includes, without limitation, physiologically or pharmacologically active substances that act locally or systemically in the body. A bioactive agent is a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, enzymes, organic catalysts, ribozymes, organometallics, proteins, glycoproteins, peptides, polyamino acids, antibodies, nucleic acids, steroidal molecules, antibiotics, antimycotics, cytokines, growth factors, carbohydrates, oleophobics, lipids, extracellular matrix and/or its individual components, pharmaceuticals, and therapeutics.

The self-crosslinkable and/or photocrosslinkable, biodegradable material may also include an accelerator. Non-limiting example accelerators include toluidines (such as N,N-diethyl-p-toluidine ("DET") and N,N-dimethyl-o-toluidine ("DMT")), acetyl phenylhydrazine, maleic acid, quinines (such as napthaquinone and anthraquinone), and alkyl mercaptans. Often, in a photocrosslinking process, an accelerator is not needed because the whole procedure is rather short (e.g., less than 30 minutes).

The self-crosslinkable and/or photocrosslinkable, biodegradable material may be used to prepare a biocompatible scaffold for tissue regeneration. The scaffold includes a biodegradable matrix formed from a block copolymer of poly (propylene fumarate) and poly(ε-caprolactone) according to the invention. The matrix may include particulate or fiber reinforcement materials such as hydroxyapatite.

The scaffold may be formed with a porogen such as crystals of sodium chloride salt or the like to be encapsulated by the polymerizing scaffold and which dissolve upon solidification of the material to form a porous scaffold. Suitable porogens include salt crystals (e.g., sodium chloride) that may be used in a salt leaching technique that forms a porous scaffold. Preferably, the porogen can be dissolved in water but not in organic solvents. Examples of this type of particle leaching technique can be found in U.S. Pat. Nos. 6,436,426, 6,379,962 and 5,514,378. The porogen may also be a hydrogel porogen as described in PCT International Publication No. WO 2005/020849. The choice of porogen may be dictated by the crosslinking process. Porogens can be used in making a crosslinked film; however, it depends the physical properties and color of the porogen. Also, some porogens may block the UV light thereby make the photocrosslinking procedure inefficient. Thus, the self-crosslinkable and/or photocrosslinkable, biodegradable material according to the invention may or may not include a porogen depending on the final product desired.

The scaffold may be formed from a block copolymer of poly(propylene fumarate) and poly(ε-caprolactone) according to the invention using various techniques. For example, a block copolymer of poly(propylene fumarate) and poly(ε-caprolactone) according to the invention may be extruded, injection molded or compression molded into a scaffold. Alternatively, solid free-form fabrication methods may also be used to form the scaffold from a block copolymer of poly(propylene fumarate) and poly(ε-caprolactone) according to the invention. Non-limiting examples of solid free-form fabrication methods include stereolithography, selective laser sintering, ballistic particle manufacturing, fusion deposition modeling, and three dimensional printing. The macrostructure and porosity of the scaffold can be manipulated by controlling printing parameters, and these features can be designed and tailored using computer assisted design (CAD) for individual patients. U.S. Pat. Nos. 6,530,958, 5,869,170, 5,518,680 and 5,490,962 provide examples of solid free-form fabrication methods. See also, Hutmacher et al., "Scaffold-based tissue engineering: rationale for computer-aided design and solid free-form fabrication systems", *Trends in Biotech.* 2004, 22(7):354. These patents and publications and all other patents and publications cited herein are incorporated herein by reference.

As used herein, a "biocompatible" material is one which stimulates only a mild, often transient, implantation response, as opposed to a severe or escalating response. As used herein, a "biodegradable" material is one which decomposes under normal in vivo physiological conditions into components which can be metabolized or excreted. As used herein, a "bioresorbable" material is one that breaks down over a finite period of time due to the chemical/biological action of the body. By "injectable", we mean the copolymer may be delivered to a site by way of a medical syringe. By "self-crosslinkable", we mean the functional groups of a polymer according to the invention may crosslink with the functional groups of the same polymer or another polymer according to the invention without a crosslinking agent that forms crosslinks between the functional groups of a polymer according to the invention and the functional groups of the same or another polymer according to the invention. By "photocrosslinkable", we mean the functional groups of a copolymer according to the invention may crosslink with the functional groups of the same polymer or another copolymer according to the invention by application of photons (e.g., UV light) in the presence of a photoinitiator.

The term "molecular weight" in this specification refers to "weight average molecular weight" ($M_w = \Sigma_i N_i M_i^2 / \Sigma_i N_i M_i$). Although weight average molecular weight ($M_w$) can be determined in a variety of ways, with some differences in result depending upon the method employed, it is convenient to employ gel permeation chromatography. As used herein, the term "number average molecular weight" ($M_n$) refers to the total weight of all the molecules in a polymer sample divided by the total number of moles present ($M_n = \Sigma_i N_i M_i / \Sigma_i N_i$). Although number average molecular weight can be determined in a variety of ways, with some differences in result depending upon the method employed, it is convenient to employ gel permeation chromatography. As used herein, the term "polydispersity" refers to the ratio of a materials' "weight average molecular weight" divided by its "number average molecular weight" ($M_w/M_n$).

EXAMPLES

The following Examples have been presented in order to further illustrate the invention and are not intended to limit the invention in any way.

A. Synthesis of P(PF-co-CL)

PCL diols[α,ω-dihydroxy poly(ε-caprolactone)] with nominal molecular weights of 530, 1250, and 2000 g·mol$^{-1}$ were purchased from Aldrich Co. (Milwaukee, Wis.) and had a chemical structure as H—[O(CH$_2$)$_5$CO—]$_m$OCH$_2$CH$_2$—O—CH$_2$CH$_2$O[—OC(CH$_2$)$_5$O]$_n$—H. Prior to copolymerization, a certain amount of PCL diol was dried overnight in a vacuum oven at 50° C. All the other chemicals in the present study were also purchased from Aldrich Co. In the first step, 259 grams of diethyl fumarate and 342 grams of 1,2-propylene glycol are mixed together in 2 L three-neck round-bottom flask with 0.33 grams of hydroquinone as a crosslinking inhibitor and 2.04 grams of zinc chloride as a polymerization catalyst. The reaction is first performed to obtain fumaric diester at 100° C. for 1 hour and then 150° C. for 7 hours. Excess of 1,2-propylene glycol and the byproduct ethanol are removed. In the second step, the intermediate is transesterified to form the linear poly(propylene fumarate) (PPF) with hydroxyl groups on both ends. The molecular weight of poly(propylene fumarate) can be modulated by varying the polymerization time. Typically the polymerization is performed under vacuum first at 100° C. and then 130° C. for 1 hour or 3 hours. After making the poly(propylene fumarate) block, the reaction is stopped by shutting off the vacuum conditions and oil bath.

To synthesize the block copolymer of poly(propylene fumarate) and poly(ε-caprolactone), 100 grams of poly(caprolactone) diol with various nominal molecular weights (typically 530, 1250, and 2000 g/mol) and 0.2 grams of antimony trioxide as a catalyst are added to the reaction vessel. After mixing completely under nitrogen at 100° C. for half an hour, the reaction temperature is raised gradually to 160° C. and a vacuum of 0 mmHg is applied. The copolymerization generally takes 5 hours and 1,2-propylene glycol was removed. The resulting block copolymer of poly(propylene fumarate) and poly(ε-caprolactone) is then purified by dissolving in methylene chloride and first washed twice by acid (600 mL 10 wt % HCl in H$_2$O for each time) to remove both catalysts. It is then purified with two washes each of both distilled water and brine. The organic phase is dried with magnesium sulfate, which is subsequently removed by vacuum filtration. The viscous solution of P(PF-co-CL) in methylene chloride obtained by rotary evaporation is precipitated in a large amount of ether. Methylene chloride and ether in the final precipitated copolymer are removed by rotary evaporation again followed by vacuum drying. The final pure product of P(PF-co-CL) is a transparent, light yellow, viscous liquid when PCL content in the copolymers is lower than 70%. Otherwise, it is wax-like at room temperature.

In Table 1, different design parameters for polymerization are shown.

TABLE 1

Different Design Parameters for Polymerization

| Run no. | Nominal molecular weight of PCL | Reaction time (hr) PPF | Reaction time (hr) Copolymer | PCL feed ratio (by wt) | PCL wt. ratio determined by NMR |
|---|---|---|---|---|---|
| 1 | 530 | 1 | 5 | 0.31 | 0.30 |
| 2 | 530 | 3 | 5 | 0.32 | 0.31 |
| 3 | 530 | 1 | 10 | 0.32 | / |
| 4 | 1250 | 1 | 5 | 0.30 | 0.32 |
| 5 | 1250 | 3 | 5 | 0.29 | 0.31 |
| 6 | 2000 | 1 | 5 | 0.31 | 0.32 |
| 7 | 2000 | 3 | 5 | 0.33 | 0.34 |
| 8 | 2000 | 1 | 5 | 0.45 | 0.46 |
| 9 | 2000 | 1 | 5 | 0.41 | 0.43 |
| 10 | 530 | 1 | 5 | 0.54 | 0.51 |
| 11 | 1250 | 1 | 5 | 0.56 | 0.54 |
| 12 | 2000 | 1 | 5 | 0.87 | 0.86 |
| 13 | 2000 | 1 | 5 | 0.81 | 0.80 |
| 14 | 2000 | 1 | 5 | 0.70 | 0.68 |
| 15 | 1250 | 1 | 5 | 0.77 | 0.75 |
| 16 | 2000 | 1 | 5 | 0.90 | 0.89 |

In Table 2, the molecular weights and physical properties of crosslinkable P(PF-co-CL) copolymers are shown.

TABLE 2

Molecular Weights and Physical Properties of P(PF-co-CL) copolymers

| Polymer | copolymer/PCL $M_w$ (dalton) | copolymer/PCL $M_n$ (dalton) | PPF $M_w$ (dalton) | PPF $M_n$ (dalton) | $T_g$ (°C.) | $T_m$ (°C.) | $\Delta H$ (J/g) | $\chi_c$ (%) | $T_d$ (°C.) | Density (g cm$^{-3}$) |
|---|---|---|---|---|---|---|---|---|---|---|
| PCL530 | 1270 | 770 | / | / | −80.6 | 26.2 | 67.5 | 50.0 | 354 | 1.073 |
| PCL1250 | 3030 | 1710 | / | / | −73.5 | 43.4 | 61.1 | 45.3 | 386 | 1.073 |
| PCL2000 | 5320 | 3970 | / | / | −68.5 | 48.7 | 76.7 | 56.8 | 392 | 1.073 |
| PPF1 hr | / | / | 1130 | 800 | −22.4 | / | / | / | 336 | 1.239 |
| PPF3 hr | / | / | 2530 | 1460 | 2.8 | / | / | / | 343 | 1.267 |
| PPF3000 | / | / | 7910 | 3460 | 24.2 | / | / | / | 351 | 1.276 |
| Copolymer 1 | 20800 | 6010 | 1300 | 810 | −22.9 | / | / | / | 350 | 1.231 |
| Copolymer 2 | 14300 | 5220 | / | / | −21.8 | / | / | / | 360 | 1.219 |
| Copolymer 3 | 21100 | 6800 | 1200 | 750 | / | / | / | / | / | / |
| Copolymer 4 | 25200 | 6180 | 1210 | 750 | −20.5 | / | / | / | 346 | 1.209 |
| Copolymer 5 | 21200 | 5590 | 2710 | 1410 | −16.9 | / | / | / | 359 | 1.206 |
| Copolymer 6 | 8230 | 4030 | / | / | −24.0 | / | / | / | 359 | 1.202 |
| Copolymer 7 | 12900 | 5530 | 1990 | 1110 | −25.3 | / | / | / | 359 | 1.206 |
| Copolymer 8 | 23200 | 8610 | 980 | 630 | −31.9 | / | / | / | 364 | 1.198 |
| Copolymer 9 | 24700 | 7440 | 1090 | 700 | −29.6 | / | / | / | 360 | 1.191 |
| Copolymer 10 | 13600 | 6730 | 1010 | 680 | −40.1 | / | / | / | 377 | 1.169 |
| Copolymer 11 | 47100 | 11600 | 1110 | 730 | −45.9 | / | / | / | 373 | 1.180 |
| Copolymer 12 | 30700 | 14300 | 1710 | 960 | −56.0 | 34.3 | 38.7 | 33.0 | 395 | 1.117 |
| Copolymer 13 | 36600 | 16100 | 1500 | 870 | −52.8 | 26.4 | 38.4 | 35.1 | 394 | 1.124 |
| Copolymer 14 | 18300 | 8570 | 1510 | 870 | −49.2 | 21.1 | 0.07 | 0.07 | 391 | 1.122 |
| Copolymer 15 | 36800 | 17200 | 900 | 620 | −53.8 | 19.7 | 6.85 | 6.59 | 392 | 1.125 |
| Copolymer 16 | 28600 | 14200 | 1640 | 950 | −57.0 | 41.8 | 48.4 | 39.8 | 396 | 1.102 |

B. Crosslinking

In a thermal-crosslinking process, benzoyl peroxide (BPO) and N-dimethyl toluidine (DMT) were used as the free radical initiator and accelerator, respectively. One hundred microliters of initiator solution (50 mg of BPO in 250 microliters of 1-vinyl-2-pyrrolidinone (NVP)) and 40 microliters of accelerator solution (20 microliters of DMT in 980 microliters of methylene chloride) were added in 1.5 grams P(PF-co-CL) solution in 500 microliters of methylene chloride and mixed thoroughly. The polymerizing scaffold was transferred into various Teflon molds and the molds were placed in a convection oven overnight to facilitate crosslinking. All the copolymers can be self-crosslinked without further adding crosslinker because of the enhanced chain flexibility after introducing PCL blocks in the backbone. After crosslinking, the crosslinked polymer was removed from the mold after it was cooled to ambient temperature. A similar crosslinking process can be done to the mixture of copolymers and porogen (salt with various size distributions) to make scaffolds with different porosity, which can be controlled by the content of porogen. After crosslinking, the salt was leached out by placing the scaffolds in distilled water for 3 days. The scaffolds were dried in vacuum for at least 12 hours.

Photocrosslinking was initiated with ultraviolet (UV) ($\lambda$=315-380 nm) using a photoinitiator bisacylphosphine oxide (BAPO, Ciba Geigy). About 75 µL of BAPO solution (30 mg BAPO in 150 mL $CH_2CH_2$) was added into 1.5 grams P(PF-co-CL) solution in 500 microliters of methylene chloride and mixed thoroughly. The mixture was poured in a mold formed by two glass plates and a Teflon spacer of 1 mm. thickness and the mold was placed directly under UV light for 30 minutes to facilitate crosslinking. Therefore, such self-crosslinkable and photo-crosslinkable copolymers are promising to construct tissue-engineering scaffolds using a variety of fabrication methods such as stereolithography.

Characterizations of materials used and copolymers produced in the Examples are shown in FIGS. 2-8.

Thus, a biodegradable block copolymer of poly(propylene fumarate) and poly($\epsilon$-caprolactone) has been developed for tissue engineering. In one specific application, this copolymer is useful as an injectable self-crosslinkable and/or photocrosslinkable material to treat skeletal defects. However, the material is not limited to treating skeletal defects, and may be used for other tissue engineering applications. The block copolymer can be crosslinked by redox or photo-initiation, with or without an additional crosslinker. Thus, the copolymer is both self-crosslinkable and photocrosslinkable.

INDUSTRIAL APPLICABILITY

The present invention relates to self-crosslinkable and/or photocrosslinkable, biodegradable polymeric materials that can be injected and then hardened in situ to form scaffolds for tissue and/or skeletal reconstruction.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A block copolymer comprising:
   caprolactone units; and
   propylene fumarate units wherein the block copolymer has the following formula:

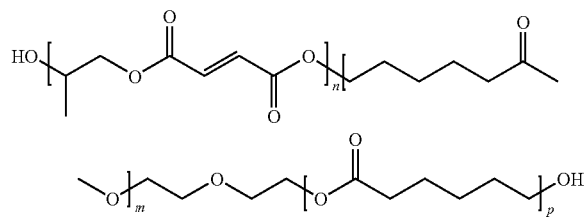

wherein n, m and p are integers.
2. The block copolymer of claim 1 wherein:
   n is 1 to 16, m is 5 to 24, and p is 5 to 24.
3. The block copolymer of claim 1 wherein:
   the block copolymer has a number average molecular weight of 5000 daltons or greater.
4. The copolymer of claim 1 wherein the copolymer is prepared by reacting (i) polycaprolactone diol and (ii) poly(propylene fumarate).
5. The copolymer of claim 4 wherein:
   the polycaprolactone diol has molecular weight in the range of 500 to 10,000 daltons.
6. A crosslinkable, biodegradable material comprising:
   the block copolymer of claim 1 wherein the propylene fumarate units comprise poly(propylene fumarate) and wherein the caprolactone units comprise poly($\epsilon$-caprolactone);
   and
   a free radical initiator or photoinitiator.
7. The material of claim 6 wherein:
   the material includes a free radical initiator, and
   the material is self-crosslinkable.
8. The material of claim 6 wherein:
   the material includes a photoinitiator, and
   the material is photocrosslinkable.
9. The material of claim 6 wherein:
   the material is injectable.
10. The material of claim 6 wherein:
    the material is a bone substitute.
11. The material of claim 6 wherein:
    the material is a bone cement.
12. The material of claim 6 further comprising:
    a porogen.
13. The material of claim 6 further comprising:
    an accelerator.
14. The material of claim 6 wherein:
    the material does not include a crosslinker.
15. The material of claim 6 further comprising:
    particulate or fiber reinforcement materials.
16. The material of claim 15 wherein:
    the reinforcement materials comprise hydroxyapatite.
17. The material of claim 6 wherein:
    the copolymer is prepared by reacting (i) poly(caprolactone) diol and (ii) poly(propylene fumarate).

* * * * *